US010859654B2

(12) United States Patent
Gulani et al.

(10) Patent No.: US 10,859,654 B2
(45) Date of Patent: Dec. 8, 2020

(54) SYSTEMS AND METHODS FOR ACCELERATION OF DICTIONARY GENERATION AND MATCHING IN PERFUSION ANALYSIS

(71) Applicant: Case Western Reserve University, Cleveland, OH (US)

(72) Inventors: Vikas Gulani, Shaker Heights, OH (US); Satyam Ghodasara, Cleveland, OH (US); Katherine Wright, Macedonia, OH (US); Nicole Seiberlich, Shaker Heights, OH (US); Mark A. Griswold, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/351,404

(22) Filed: Mar. 12, 2019

(65) Prior Publication Data

US 2019/0285712 A1    Sep. 19, 2019

Related U.S. Application Data

(60) Provisional application No. 62/642,388, filed on Mar. 13, 2018.

(51) Int. Cl.
*G01R 33/56* (2006.01)
*G01R 33/563* (2006.01)
(Continued)

(52) U.S. Cl.
CPC ......... *G01R 33/5602* (2013.01); *A61B 5/055* (2013.01); *G01R 33/5601* (2013.01);
(Continued)

(58) Field of Classification Search
CPC .......... G01R 33/5602; G01R 33/56308; G01R 33/5601; G01R 33/443; G01R 33/281;
(Continued)

(56) References Cited

U.S. PATENT DOCUMENTS

| 8,723,518 B2 | 5/2014 | Seiberlich |
| 2008/0139920 A1* | 6/2008 | Biglieri ................. A61B 5/055 |
| | | 600/410 |

(Continued)

OTHER PUBLICATIONS

Bultman, Eric M., et al. "Quantitative hepatic perfusion modeling using DCE-MRI with sequential breathholds." Journal of Magnetic Resonance Imaging 39.4 (2014): 853-865.
(Continued)

*Primary Examiner* — G. M. A Hyder
(74) *Attorney, Agent, or Firm* — Quarles & Brady LLP

(57) ABSTRACT

A method for determining quantitative parameters for dynamic contrast-enhanced MR data includes acquiring a set of contrast-enhanced MR data for a region of interest using a T1-weighted pulse sequence, generating at least one contrast concentration curve based on the set of contrast-enhanced MR data, accessing a comprehensive dictionary of contrast concentration curves and generating a grouped dictionary that has a plurality of groups based on the comprehensive dictionary. Each group includes a plurality of correlated contrast concentration curves and a group representative signal for the group. The method also includes comparing a contrast concentration curve with the group representative signal of each group to select a group, comparing the contrast concentration curve to the plurality of correlated contrast concentration curves in the selected group to identify a set of quantitative parameters for the concentration curve and generating a report including the set of quantitative parameter.

21 Claims, 9 Drawing Sheets

(51) Int. Cl.
*A61B 5/055* (2006.01)
*G01R 33/28* (2006.01)
*G01R 33/44* (2006.01)

(52) U.S. Cl.
CPC ...... *G01R 33/56308* (2013.01); *G01R 33/281* (2013.01); *G01R 33/443* (2013.01)

(58) Field of Classification Search
CPC . G01R 33/56366; A61B 5/055; G06T 7/0012; G06T 2207/20084; G06T 2207/30104; G06T 2207/10096
See application file for complete search history.

(56) References Cited

U.S. PATENT DOCUMENTS

| | | | | |
|---|---|---|---|---|
| 2008/0194943 | A1* | 8/2008 | Lorenz | A61B 5/0263 600/419 |
| 2010/0274119 | A1* | 10/2010 | Kabasawa | A61B 5/0263 600/420 |
| 2015/0301141 | A1 | 10/2015 | Griswold | |
| 2015/0309141 | A1* | 10/2015 | Kim | G01R 33/5601 600/416 |
| 2017/0325709 | A1* | 11/2017 | Nayak | A61B 5/055 |
| 2019/0056470 | A1* | 2/2019 | Wang | G01R 33/5608 |

OTHER PUBLICATIONS

Cauley SF, et al. Fast group matching for MR fingerprinting reconstruction. Magnetic Resonance in Medicine. 2014;74(2):523-528. doi:10.1002/mrm.25439.

Chen, Y et al., "Free-breathing liver perfusion imaging using 3D through-time spiral GRAPPA acceleration." Investigative radiology 50.6 (2015): 367.

Ma, D., et al., in "Magnetic Resonance Fingerprinting," Nature, 2013; 495(7440):187-192.

Materne, Roland, et al. "Non-invasive quantification of liver perfusion with dynamic computed tomography and a dual-input one-compartmental model." Clinical Science 99.6 (2000): 517-525.

Yang, M, et al., "Low rank approximation methods for MR fingerprinting with large scale dictionaries." Magnetic resonance in medicine 79.4 (2018): 2392-2400.

* cited by examiner

SYSTEMS AND METHODS FOR ACCELERATION OF DICTIONARY GENERATION AND MATCHING IN PERFUSION ANALYSIS

CROSS-REFERENCE TO RELATED APPLICATION

This application is based on, claims priority to, and incorporates herein by reference in its entirety U.S. Ser. No. 62/642,388 filed Mar. 13, 2018, and entitled "Acceleration of Dictionary Generation And Matching in Perfusion Analysis."

GOVERNMENT FUNDING STATEMENT

This invention was made with government support under R01DK098503 and R01EB016728 awarded by the National Institutes of Health. The government has certain rights in the invention.

BACKGROUND

Dynamic contrast-enhanced magnetic resonance imaging (DCE-MRI) monitors the transit of a contrast agent (e.g., gadolinium (Gd) or other paramagnetic material) through a region of interest (e.g., a tissue or a tumor). DCE-MRI may be used to evaluate cancer or other diseases and may be performed on any organ, for example, the brain, heart, liver, prostate and kidney. DCE-MRI techniques acquire T1-weighted images (or data) that may be used to characterize tissue perfusion properties such as, for example, blood flow, perfusion, blood volume and mean transit time. During a DCE-MRI study, T1-weighted images are acquired before, during and after the intravenous administration of the contrast agent which results in the acquisition of a time sequence of images that track the passage of the contrast agent through the region of interest. The presence of the contrast agent in the vessel and tissue shortens T1 relaxation and effects the MR signal intensity (e.g., increases or brightens the signal intensity) depending on the local concentration of the contrast agent.

Quantitative analysis of the acquired images may be performed using a pharmacokinetic model to estimate clinically relevant parameters such as, for example, the transfer rate constant, $K^{trans}$, the fraction of plasma per unit volume of tissue, $V_p$, and the extracellular extravascular volume fraction, $V_e$. For example, contrast agent concentration curves may be computed from the acquired images. A curve-fitting technique may then be used to fit the pharmacokinetic model to the measured contrast agent concentration curves to determine the quantitative parameters. There are, however, drawbacks to using a curve-fitting technique. For example, curve-fitting techniques have many configuration options including initial values, algorithm choice, tolerances, and cost functions. Curve-fitting is also prone to converging on local minima for complex models and can require significant time to generate perfusion maps.

It would be desirable to provide systems and methods to improve the speed, efficiency and accuracy of analyzing DCE-MRI data to determine quantitative parameters.

SUMMARY OF THE DISCLOSURE

In accordance with an embodiment, a method for determining quantitative parameters for dynamic contrast-enhanced magnetic resonance (MR) data includes acquiring a set of contrast-enhanced MR data for a region of interest using a T1-weighted pulse sequence, generating at least one contrast concentration curve based on the set of contrast-enhanced MR data, accessing a comprehensive dictionary of contrast concentration curves and generating a grouped dictionary based on the comprehensive dictionary. The grouped dictionary includes a plurality of groups, where each group includes a plurality of correlated contrast concentration curves and a group representative signal that represents the group. The method also includes comparing at least one contrast concentration curve with the group representative signal of each group to select a group, comparing the at least one contrast concentration curve to the plurality of correlated contrast concentration curves in the selected group to identify at least one quantitative parameter for the at least one contrast concentration curve and generating a report including the at least one quantitative parameter.

In accordance with another embodiment, a method for determining quantitative parameters for dynamic contrast-enhanced magnetic resonance (MR) data includes acquiring a set of contrast-enhanced MR data for a region of interest using a T1-weighted pulse sequence, generating at least one contrast concentration curve based on the set of contrast-enhanced MR data and accessing a compressed dictionary. The compressed dictionary is generated by performing a randomized singular value decomposition on a dictionary of concentration curves. The compressed dictionary comprises a series of singular values from the dictionary of concentration curves. The method also includes comparing at least one contrast concentration curve with the compressed dictionary to identify at least one quantitative parameter for the at least one contrast concentration curve and generating a report including the at least one quantitative parameter.

In accordance with another embodiment, a method for determining quantitative parameters for dynamic contrast-enhanced magnetic resonance (MR) data includes acquiring a set of contrast-enhanced MR data for a region of interest using a T1-weighted pulse sequence, generating at least one contrast concentration curve based on the set of contrast-enhanced MR data, providing at least one concentration curve to a neural network, the neural network trained using a dictionary of contrast concentration curves, generating at least one quantitative parameter for the at least one contrast concentration curve using the neural network and generating a report including the at least one quantitative parameter.

In accordance with another embodiment, a magnetic resonance imaging system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array and a computer system comprising a graphics processing unit. The computer system is programmed to access a dictionary of concentration curves, acquire a set of contrast-enhanced MR data for a region of interest using a T1-weighted pulse sequence, generate at least one contrast concentration curve based on the set of contrast-enhanced MR data and using the graphics processing unit, compare at least one contrast concentration curve with the dictionary to identify at least one quantitative parameter for the at least one contrast concentration curve. The comparison is performed as a plurality of operations, each operation performed independently and simultaneously by the graphics processing unit. The computer system is also programmed to generate a report including the at least one quantitative parameter.

BRIEF DESCRIPTION OF THE DRAWINGS

The present invention will hereafter be described with reference to the accompanying drawings, wherein like reference numerals denote like elements.

DETAILED DESCRIPTION

Figure 1:
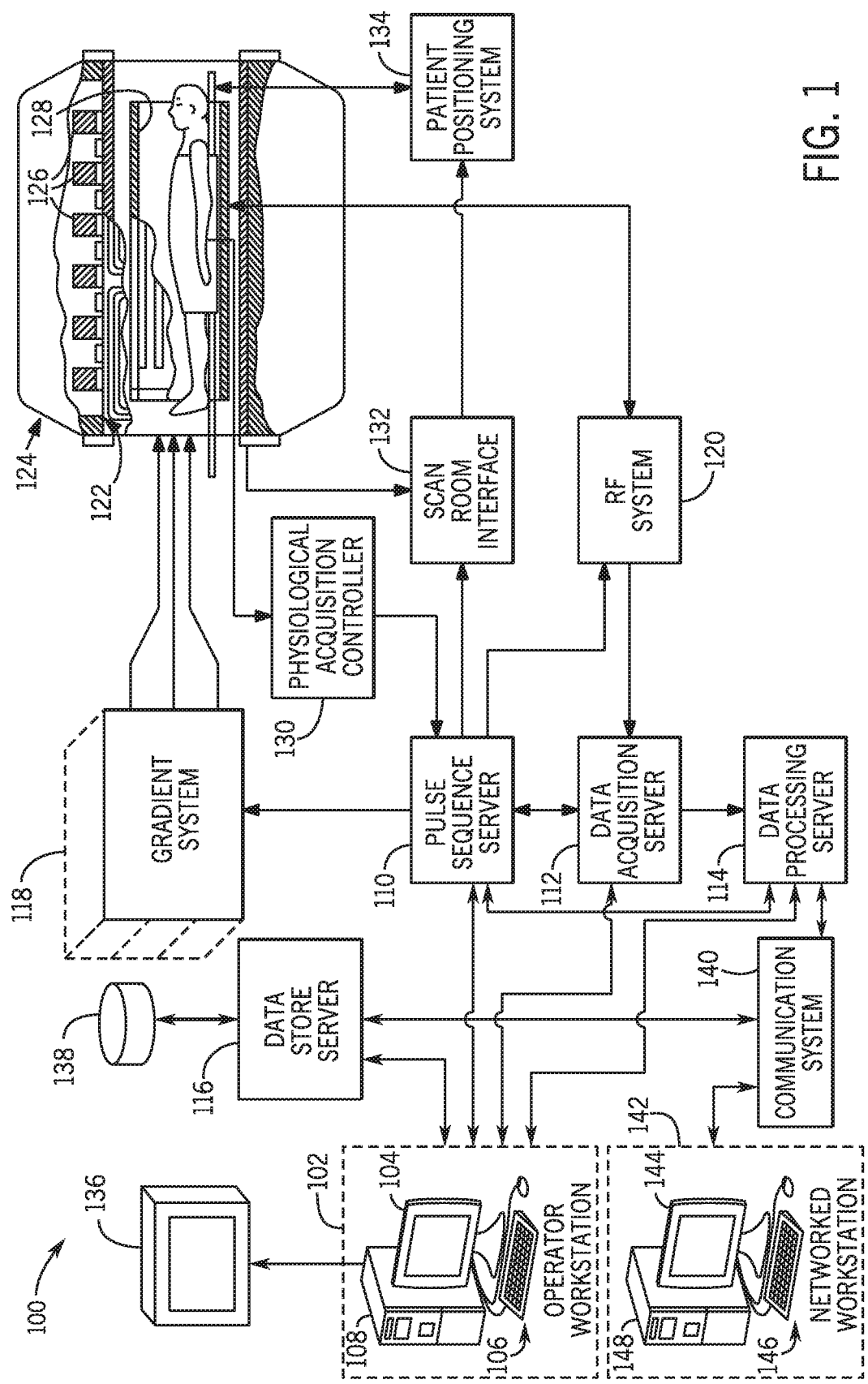
FIG. 1 is a schematic diagram of an example MRI system in accordance with an embodiment.

FIG. 1 shows an example of an MRI system 100 in accordance with an embodiment. MRI system 100 may be used to implement the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

Figure 2:
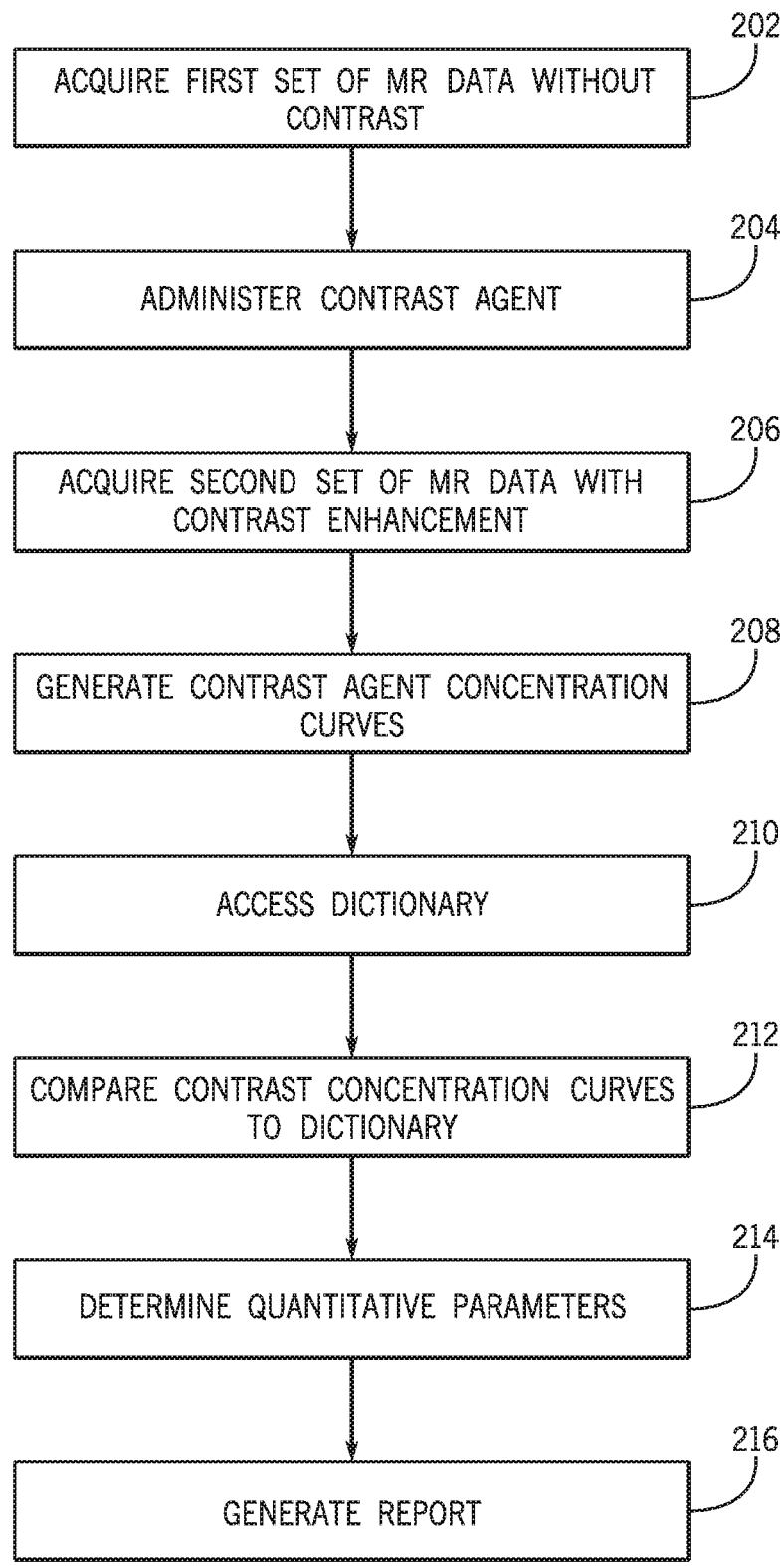
FIG. 2 illustrates a method for dynamic contrast-enhanced magnetic resonance imaging (DCE-MRI) and perfusion analysis using dictionary matching in accordance with an embodiment.

The MRI system 100 of FIG. 1 may be used to acquire DCE-MRI data and images and to perform perfusion analysis. In another embodiment, DCE-MRI data acquired using a MRI system (e.g., MRI system 100) may be analyzed using a computer system. FIG. 2 illustrates a method for dynamic contrast-enhanced magnetic resonance imaging (DCE-MRI) and perfusion analysis using dictionary matching in accordance with an embodiment. At block 202, a first set of MR data (or images) is acquired without a contrast agent using a T1-weighted pulse sequence such as, for example, a T1-weighted fast spoiled gradient echo sequence. An MRI system (e.g., MRI system 100 show in FIG. 1) may be used to acquire the first set of MR data from a tissue in a region of interest in a subject. In another embodiment, the first set of MR data may be otherwise provided. For example, the first set of MR data can already be acquired and thus can be provided by retrieving the already acquired data from storage. The first set of MR data may be used as baseline image(s) without contrast enhancement. The first set of MR data may be used to estimate a baseline T1 that may be used to, for example, enable transformation of a signal-intensity time curve into a time concentration curve as discussed further below. At block 204, a contrast agent bolus is administered to a subject, The contrast agent is a paramagnetic material such as, for example, gadolinium (Gd). The contrast agent may be administered by, for example, intravenous injection into the subject. After injection, the contrast agent resides in plasma and is circulated to tissues in proportion to blood flow.

At block 206, after administration of the contrast agent to the subject a second set of MR data (or images) is acquired with contrast enhancement. The second set of MR data includes a series of images acquired over time (e.g., up to 5-10 minutes) during and after arrival of the contrast agent in tissue in the region of interest. In an embodiment, the series of images may be acquired by applying a T1-weighted pulse sequence repeatedly, e.g., every few seconds. The T1-weighted sequence may be, for example, a 3D T1-weighted fast spoiled gradient echo sequence. As the contrast agent enters and disperses through the tissue in the region of interest, it alters the MR signal intensity of the tissue depending on its local concentration. Accordingly, the series of images acquired after contrast agent injection may display a higher signal intensity indicating the presence of the contrast agent. Changes in the contrast agent concentration effect the signal intensity in a non-linear manner. An MRI system (e.g., MRI system 100 shown in FIG. 1) may be used to acquire the second set of MR data from a tissue in a region of interest in a subject. In another embodiment, the second set of MR data may be otherwise provided. For example, the second set of MR data can already be acquired and thus can be provided by retrieving the already acquired data from storage. At block 208, a set of contrast concentration curves is generated based at least on the second set of MR data. In one embodiment, a contrast concentration is calculated for each voxel over time in the dynamic image series of the second set of MR data. The concentration of the contrast agent may be determined from the magnitude of the MR signal (e.g., a signal intensity curve). For example, each signal intensity curve may be converted to contrast concentration (unit mM) using a spoiled gradient echo signal equation. In another embodiment, an arterial input function (AIF) may also be calculated using known methods.

At block 210, a dictionary of contrast concentration curves and associated quantitative parameters is accessed. As used herein, the term "accessing" may refer to any number of activities related to generating, retrieving or processing the dictionary using, for example, MRI system 100 (shown in FIG. 1), an external network, information repository, or combinations thereof. The dictionary may be stored in memory or data storage of, for example, an MRI system (e.g., the MRI system 100 of FIG. 1) or other computer system. The "known" contrast concentration curves may be, for example, simulated concentration curves calculated from a pharmacokinetic model and/or previously acquired concentration curves. Each entry in the dictionary corresponds with a set of quantitative parameters (e.g., transfer constants, volume fractions, blood flow, permeability, arterial function, mean transit time, etc.). For example, a range of parameter values may be used to simulate the concentration curves in the dictionary. At block 212, the measured concentration curves are compared to the dictionary to match the measured concentration curves with concentration curves stored in the dictionary. This comparison allows estimation of quantitative parameters for the measured concentration curves and the associated tissue or other material in the region of interest. As an example, the comparison of the measured concentration curves to a dictionary can be performed using any suitable matching or pattern recognition technique (e.g., pattern matching, template matching). The parameters for the tissue or other material in a given voxel may be estimated to be the values that provide the best template matching. In one embodiment, the acquired concentration curves may be matched to the dictionary by identifying the maximum correlation coefficient.

At block 214, one or more quantitative parameters of the measured concentration curves are determined based on the comparison and matching at block 212. For example, from the dictionary index the set of perfusion properties used to generate the dictionary entry may be obtained. The parameters may include, for example, influx mass transfer rate of contrast agent ($K^{trans}$) reflux rate of contrast agent ($K_{ep}$), the extracellular extravascular space (EES) volume fraction ($V_e$), fractional volume of plasma ($V_p$), vascular permeability, surface area, blood flow, and mean transit time. The one or more quantitative parameters may indicate the functional status of the vascular system within tissues or other material in the region of interest. In an embodiment, each of the concentration curves generated at block 208 is compared to the dictionary at block 212 to identify at least one quantitative parameter for the contrast concentration curve. At block 216, a report may be generated indicating at least one of the identified quantitative parameters for the tissue in a region of interest in a subject. The report may include, for example, images or maps, text or metric based reports, audio reports and the like. The report may be provided to a display (e.g., display 104, 136 or 144 shown in FIG. 1).

Figure 3:
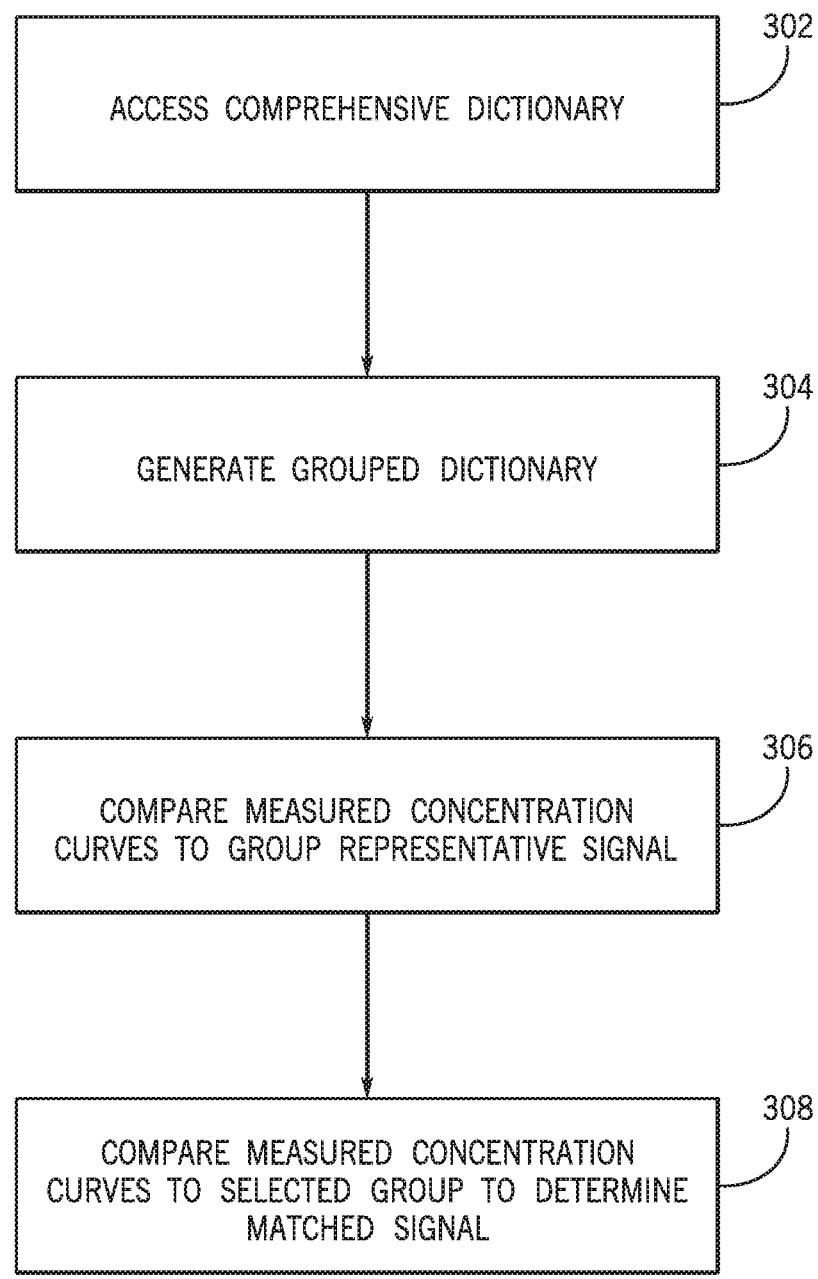
FIG. 3 illustrates a method for dictionary matching using fast group matching in accordance with an embodiment.

As mentioned above, the measured contrast concentration curves are compared to a dictionary of contrast concentration curves to identify a match with an entry in the dictionary at block 212 and identify one or more quantitative parameters at block 214. A fast group matching technique may be used to improve performance (e.g., computational efficiency) of the dictionary matching process described above for use in perfusion analysis of DCE-MRI data. Methods and apparatus employing fast group matching may improve on conventional approaches by leveraging techniques from discrete optimization and numerical linear algebra to take advantage of the correlated nature of dictionary elements and to reduce the time involved in matching measured signals against a dictionary. FIG. 3 illustrates a method for dictionary matching using fast group matching in accordance with an embodiment. At block 302, a comprehensive dictionary of contrast concentration curves is accessed. The concentration curves stored in the comprehensive dictionary may be from previous acquisitions, may be derived from theoretical models (e.g., pharmacokinetic models), or may be a combination of previous acquisitions and theoretical models. At block 304, a grouped dictionary is generated based on the comprehensive dictionary. The grouped dictionary includes a plurality of groups, where each group includes similar data. In one embodiment, a group includes a plurality of correlated concentration curves, a group representative signal that represents the group and a group low-rank representative. A group representative signal may be generated by determining the mean signal across the group, or may be calculated using statistics-based estimations. In other embodiments, other techniques may be used to generate the group representative signal.

At block 306, the measured concentration curves are compared with the group representative signals to match the measured concentration curves with a group representative signal. In one embodiment, the number of groups under consideration are restricted to an integer greater than or equal to one. The number of groups under consideration may be a threshold number of groups less than the total number of groups. The threshold number of groups may be adapted automatically and dynamically, based on the results of current matching operations, changes in the grouped dictionary composition, changes in the acquired MR data, and for other reasons. In an embodiment, if the measured concentration curves cannot be matched to the representative signal for a group within a threshold percentage of a best option match, that group may be pruned from consideration and no longer searched for matching concentration curves. In another embodiment, the next best option within a group, or a threshold number of next best options within a group may be considered to determine if a stable point has been reached. At block 308, the measured concentration curve is compared to the group associated with the group representative signal providing the best match at block 306. The comparison determines the concentration curve within the group that provides the best match to the measured data. In one embodiment, the matched concentration curve may be selected by matching to within a threshold quality of fit, the measured concentration curve with a concentration curve in the selected group. In one embodiment, the matching is based on a group low-rank representative determined by a principal component analysis (PCA) of the grouped dictionary. In one example, the threshold quality of fit is a dynamic, adaptive threshold. In another example, other qualities of fit may be employed.

Figure 4:
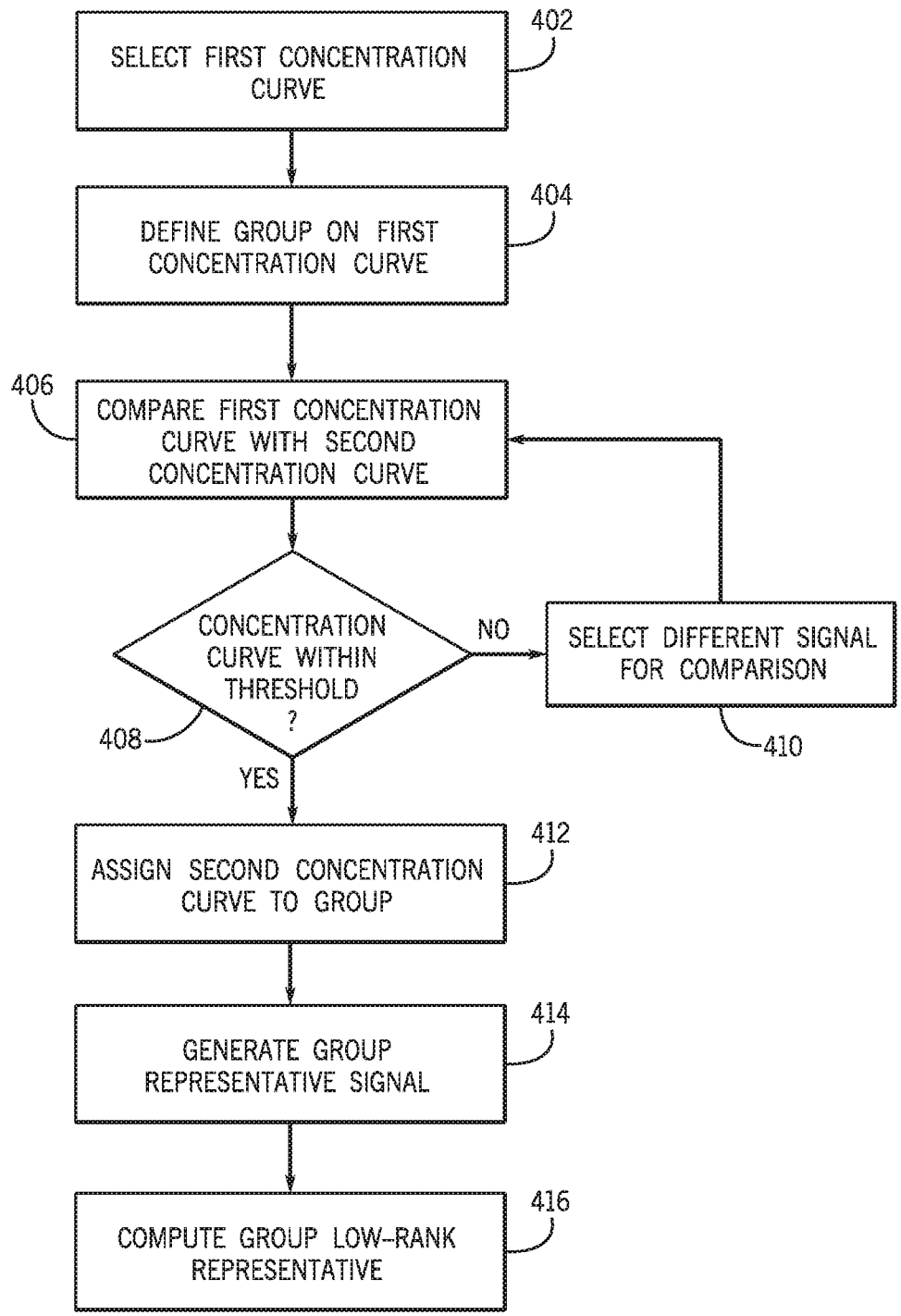
FIG. 4 illustrates a method for generating a grouped dictionary for fast group matching in accordance with an embodiment.

FIG. 4 illustrates a method for generating a grouped dictionary for fast group matching in accordance with an embodiment. At block 402, a first contrast concentration curve is selected from a comprehensive dictionary. In one embodiment, selecting a first concentration curve from the comprehensive dictionary includes randomly selecting a concentration curve from the comprehensive dictionary, or selecting a mean concentration curve for a tissue type represented in the comprehensive dictionary. In another embodiment, other approaches may be used to select the first concentration curve. At block 404, a group is defined based on the first concentration curve. The group includes the first concentration curve. A group may be defined using a threshold correlation value.

At block 406, the first concentration curve is compared with a second, different concentration curve selected from the comprehensive dictionary. In an embodiment, comparing the first concentration curve with the second concentration curve may include computing a correlation between the first concentration curve and the second concentration curve. At block 408, it is determined whether the second concentration curve is within a threshold correlation of the first concentration curve. At block 410, upon determining that the second concentration curve is not within a threshold correlation of the first concentration curve, a different concentration curve is selected from the comprehensive dictionary to compare to the first signal. In one embodiment, determining that the second concentration curve is not within a threshold correlation of the first concentration curve is a function of sparse methods including K-way partitioning, or greedy choice grouping. In one example, K-way partitioning repetitively solves minimum cut problems to sub-divide elements hierarchically. K-way partitioning may be employed for smaller data sets. In a k-way partitioning example, highly scalable greedy grouping schemes may be used for larger data sets. In other embodiments, other techniques may be employed to determine if the second concentration curve is not within a threshold correlation of the first MRF signal evolution.

At block 412, upon determining that the second concentration curve is within the threshold correlation of the first concentration curve, the second concentration curve is assigned to the group. In one embodiment, determining that the second concentration curve is within the threshold correlation of the first concentration curve is a function of sparse methods including K-way partitioning, or greedy choice grouping. In another embodiment, the determination may be made using other statistical or pattern matching approaches.

At block 414, a group representative signal for the group is generated. In one embodiment, generating the group representative signal for the group includes calculating the mean signal across the plurality of correlated concentration curves in the group. In one embodiment, the group representative signal may be generated by calculating a statistics-based estimation from the plurality of correlated concentration curves in the group. In one embodiment, outlying correlated concentration curves may be excluded from the calculation of the mean signal. In some embodiments, the representative signals are used by example methods and apparatus to disqualify poorly matching groups from further matching consideration. Disqualifying poorly matching groups from further consideration reduces the computational resources used to complete the matching operation. At block 416, a group low-rank representative for the group is computed. In one embodiment, computing the group low-rank representative may be based, at least in part, on a PCA approach using singular value decomposition.

In one embodiment, the grouped dictionary includes all the elements of the comprehensive dictionary. In another embodiment, the grouped dictionary includes a subset of the elements of the comprehensive dictionary that contains less than all the elements of the comprehensive dictionary. The size of the subset is based, at least in part, on a stopping criterion. The stopping criterion may be, for example, a threshold number of grouped elements in the grouped dictionary. In one embodiment, when a threshold number of grouped elements are in the grouped dictionary, the process may terminate. The stopping criterion may be adjusted automatically and dynamically to adjust for changing computing resources, accuracy, clinical conditions, and other reasons. If additional grouping is desired, the process may select more ungrouped concentration curves from the comprehensive dictionary and repeat the grouping process. In another embodiment, the grouped dictionary includes a number M of concentration curves, where M is an integer greater than 1, and where the M concentration curves are evenly spread across a number N groups. In this case, N is an integer greater than 0. In still another embodiment, the grouped dictionary includes a number M of concentration curves, where M is an integer greater than 1. In this embodiment, the M concentration curves are spread unevenly across a number N groups, where N is an integer greater than 0. In other embodiments, the M concentration curves may be spread across the number N groups according to other distributions, including, for example, normal, binomial, or trinomial.

Figure 5:
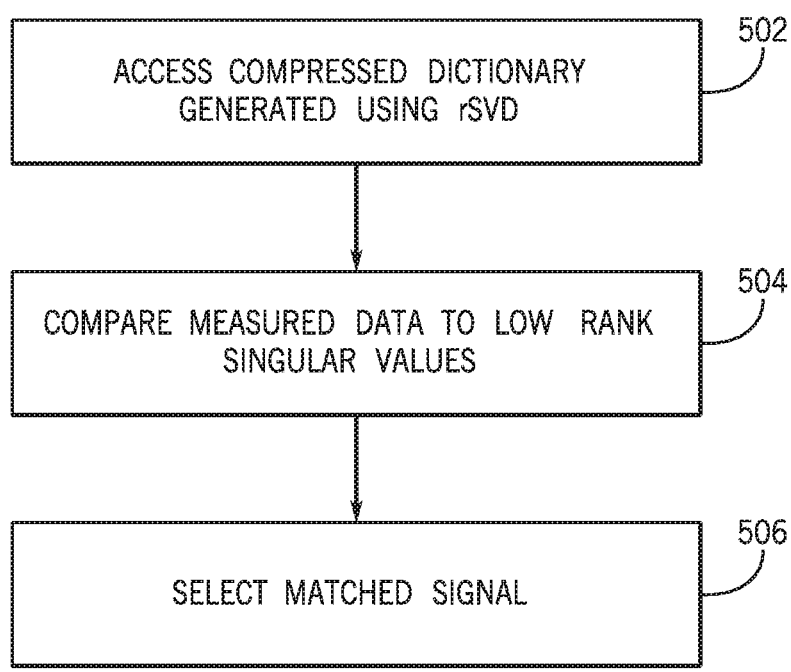
FIG. 5 illustrates a method for dictionary matching using a compressed dictionary in accordance with an embodiment.

In another embodiment, a compressed dictionary using a low rank dictionary approximation may be used to improve performance (e.g., computational efficiency, reduced memory requirements) of the dictionary matching process described above for use in perfusion analysis of DCE-MRI data. FIG. 5 illustrates a method for dictionary matching using a compressed dictionary in accordance with an embodiment. At block 502, a compressed dictionary is generated using randomized singular value decomposition (rSVD) on a dictionary of concentration curves. The singular values obtained from applying the rSVD to each entry of the dictionary are stored as low rank approximations of the true values. At block 504, the measured concentration curves are compared to the low rank singular values to match the measured concentration curves with a low rank singular value which represents a dictionary entry. Comparing the concentration curves to the compressed dictionary may be performed in a number of ways, such as using a pattern or matching algorithm. At block 506, the concentration curve associated with the matched low rank singular values is selected.

Figure 6:
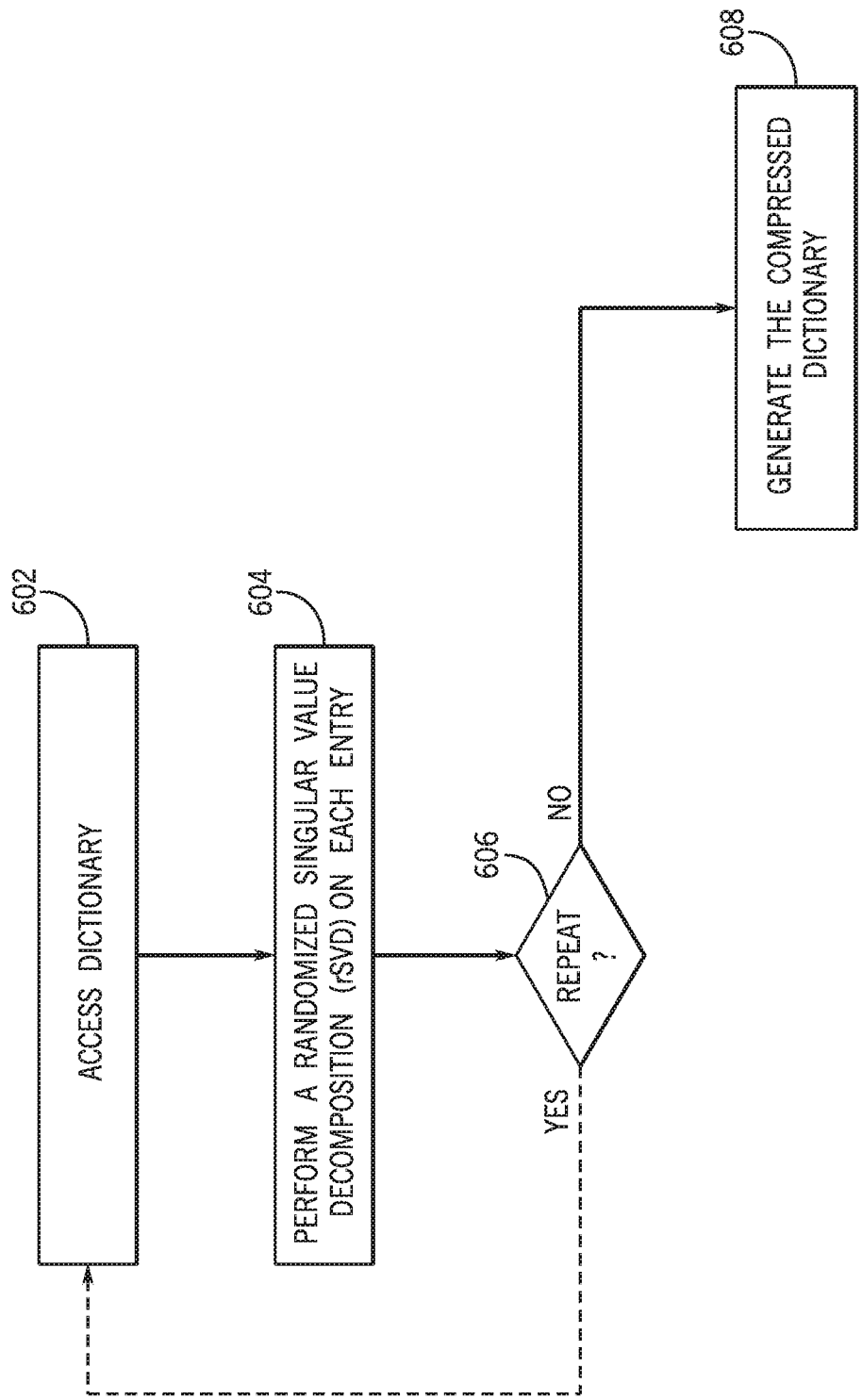
FIG. 6 illustrates a method for generating a compressed dictionary from a randomized singular value decomposition (rSVD) in accordance with an embodiment.

FIG. 6 illustrates a method for generating a compressed dictionary from a randomized singular value decomposition (rSVD) in accordance with an embodiment. The method is used to, for example, reduce the memory requirement of the concentration curve dictionary. At block 602, a dictionary of concentration curves is accessed. The concentration curves stored in the comprehensive dictionary may be from previous acquisitions, may be derived from theoretical models (e.g., pharmacokinetic models), or may be a combination of previous acquisitions and theoretical models. At block 604, a randomized singular value decomposition (rSVD) is performed on each entry of the dictionary. The singular value obtained from applying the rSVD to the dictionary entry is stored as low rank approximations of the true value. This process may be optionally repeated at block 506 by performing a second rSVD on a second concentration curve, or the process may be stopped to generate the compressed dictionary at block 608. Method steps 602-606 may be repeated any number of times to generate the compressed dictionary. Unlike conventional SVD, the rSVD process allows for the compressed dictionary to be generated on-the-fly (e.g., generating the compressed dictionary at the same time as portions of the dictionary are being acquired/simulated). Therefore, this process avoids having to store the entire dictionary in the memory of a computer.

Figure 7:
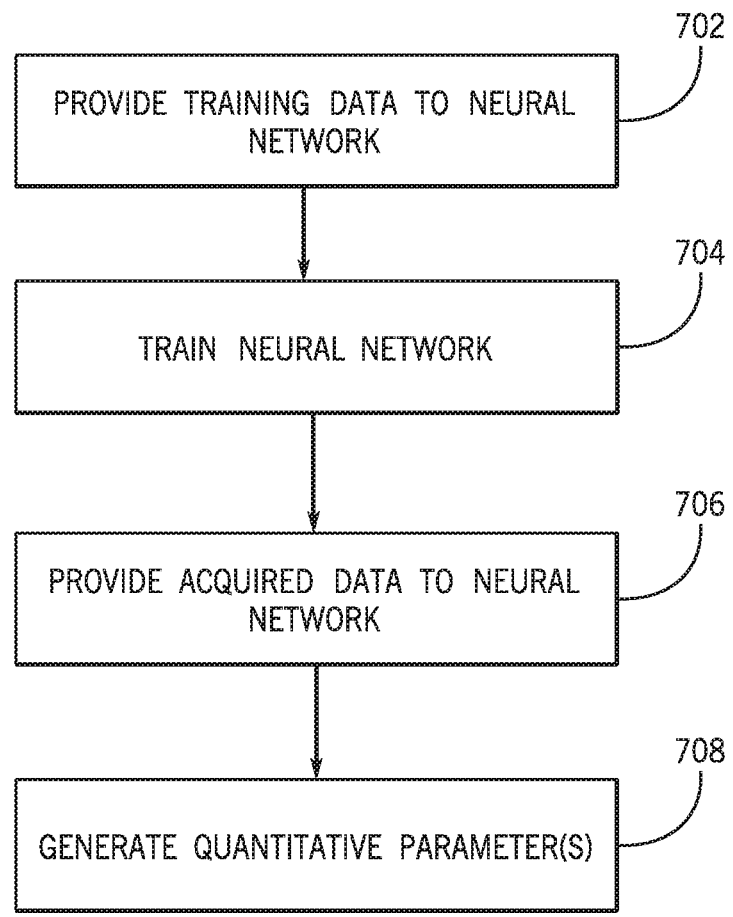
FIG. 7 illustrates a method for dictionary matching using an unsupervised learning model in accordance with an embodiment.
Figure 8:
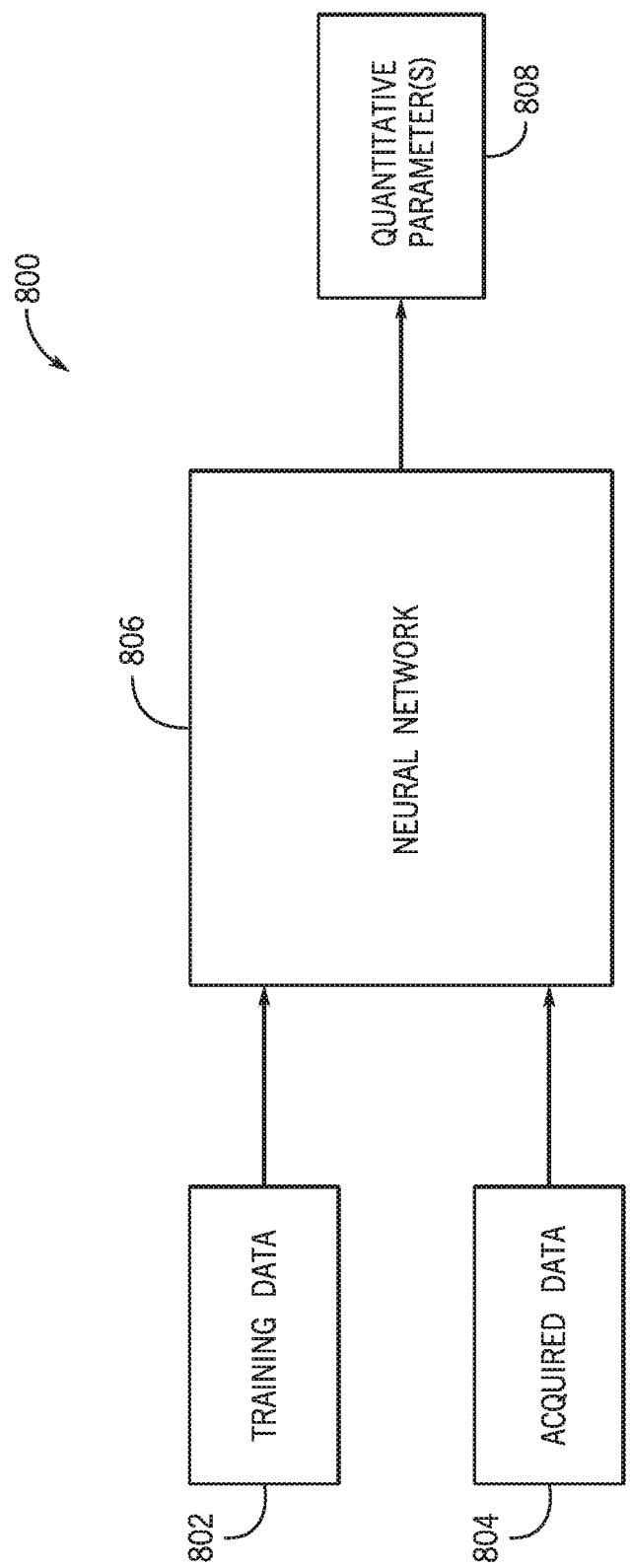
FIG. 8 is a block diagram of an example neural network for dictionary matching in accordance with an embodiment.

In another embodiment, machine learning methods may be used to improve performance (e.g., computational efficiency and accuracy) of the dictionary matching process described above for use in perfusion analysis of DCE-MRI data. FIG. 7 illustrates a method for dictionary matching using a neural network in accordance with an embodiment and FIG. 8 is a block diagram of an example neural network for dictionary matching in accordance with an embodiment. Referring to FIGS. 7 and 8, at block 702 training data 802 is provided to a neural network 806. In one embodiment, training data 802 is a dictionary of contrast concentration curves or a subset of entries from a dictionary of contrast concentration curves. The neural network 806 may be configured as a supervised learning model or unsupervised learning model. At block 704, the dictionary (i.e., training data 802) is used to train the neural network to derive associated properties, e.g., quantitative parameters associated with a concentration curve. Once the neural network 806 has been trained using the dictionary on concentration curves, measured concentration curves 804 may be provided to the neural network at block 706. At block 708, the trained neural network 806 will generate the properties, e.g., quantitative parameters, associated with the measured concentration curves 804.

In another embodiment, GPU hardware and parallel computing techniques may be used to improve performance (e.g., computational efficiency) of the dictionary matching process described above for use in perfusion analysis of DCE-MRI data. GPU hardware and parallel computing techniques may also be used to accelerate dictionary generation. A GPU may be used for parallel processing and is capable of performing the same kind of task multiple times. In various embodiments, dictionary matching is essentially a matrix multiplication operation. The matrix multiplication operation for dictionary matching may be divided into multiple smaller matrix multiplication operations that may be performed independently and simultaneously using a GPU. As mentioned above, a dictionary of concentration curves for perfusion analysis may be generated by simulating a plurality of concentration curves using a pharmacokinetic model. Each entry in the dictionary is independent and may be calculated simultaneously. In an embodiment, each thread available on a GPU may be used to calculate one concentration curve (e.g., a dictionary entry) simultaneously.

Figure 9:
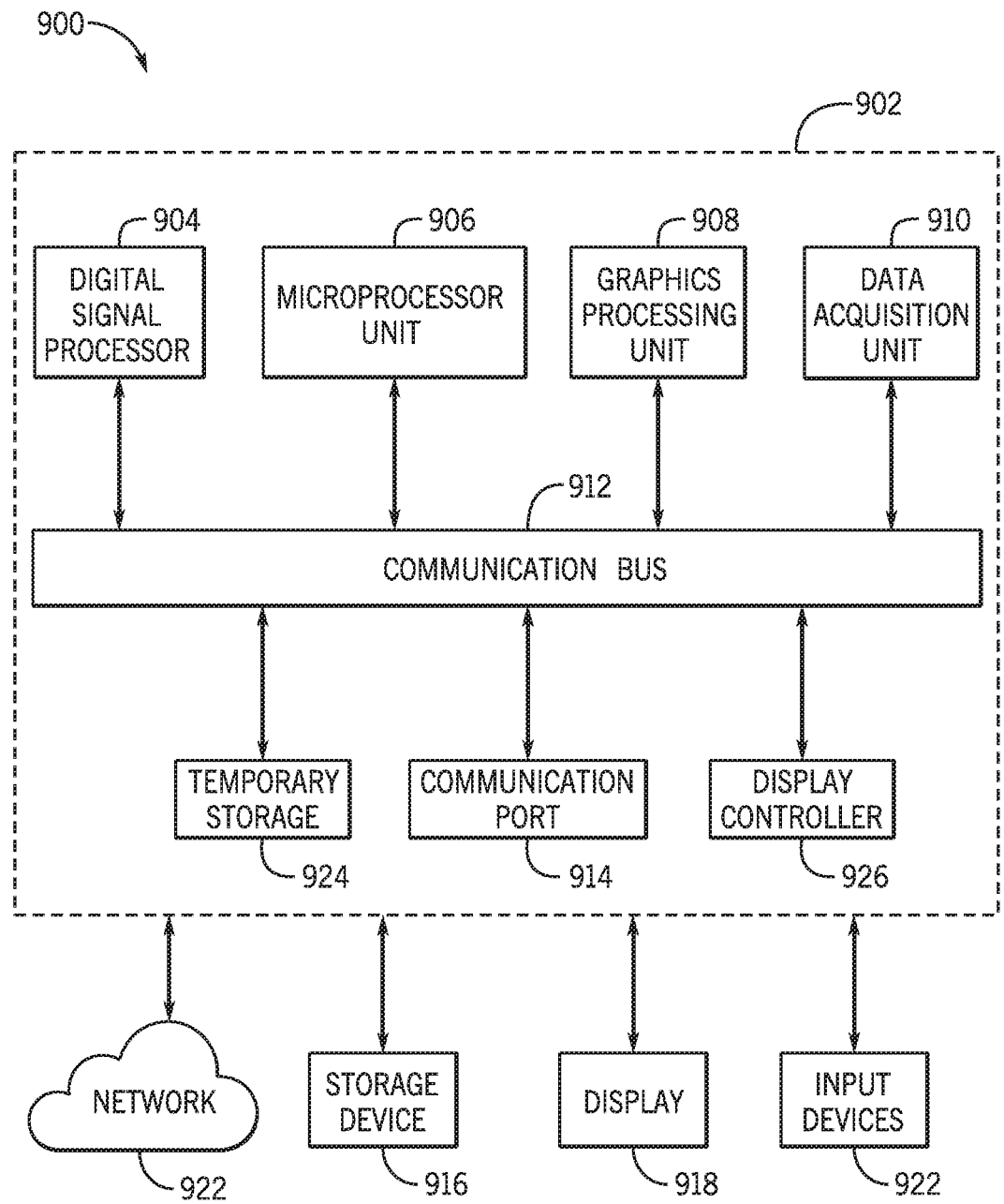
FIG. 9 is a block diagram of an example computer system including a graphics processing unit (GPU) in accordance with an embodiment.

FIG. 9 is a block diagram of an example computer system including a graphics processing unit (GPU) in accordance with an embodiment. Computer system 900 may be used to implement the methods described herein. In some embodiments, the computer system 900 may be a workstation, a notebook computer, a tablet device, a mobile device, a multimedia device, a network server, a mainframe, one or more controllers, one or more microcontrollers, or any other general-purpose or application-specific computing device. The computer system 900 may operate autonomously or semi-autonomously, or may read executable software instructions from the memory or storage device 916 or a computer-readable medium (e.g., a hard drive, a CD-ROM, flash memory), or may receive instructions via the input device 922 from a user, or any other source logically connected to a computer or device, such as another networked computer or server. Thus, in some embodiments, the computer system 900 can also include any suitable device for reading computer-readable storage media.

Data, such as data acquired with an MRI system (e.g., MRI system 100 shown in FIG. 1), may be provided to the computer system 900 from a data storage device 916, and these data are received in a processing unit 902. In some embodiment, the processing unit 902 includes one or more processors. For example, the processing unit 902 may include one or more of a digital signal processor (DSP) 904, a microprocessor unit (MPU) 906, and a graphics processing unit (GPU) 908. The processing unit 902 also includes a data acquisition unit 910 that is configured to electronically receive data to be processed. The DSP 904, MPU 906, GPU 908, and data acquisition unit 910 are all coupled to a communication bus 912. The communication bus 912 may be, for example, a group of wires, or a hardware used for switching data between the peripherals or between any component in the processing unit 902.

The DSP 904 may be configured to implement the methods described here. The MPU 906 and GPU 908 may also be configured to implement the method described here in conjunction with the DSP 904. For example, the MPU 906 may be configured to control the operation of components in the processing unit 902 and can include instructions to implement the methods described in the present disclosure, including implementing one or more machine learning algorithms to estimate quantitative magnetic resonance parameters, as described above, on the DSP 804. In an embodiment, the GPU 908 is configured to perform a dictionary matching process as described above by independently and simultaneously performing multiple matrix multiplication operations. In another embodiment, the GPU 908 is configured to perform a dictionary generation process as described above by calculating multiple dictionary entries independently and simultaneously. For example, each thread available on a GPU may be used to calculate one dictionary entry simultaneously.

The processing unit 902 may also include a communication port 914 in electronic communication with other devices, which may include a storage device 916, a display 918, and one or more input devices 920. Examples of an input device 920 include, but are not limited to, a keyboard, a mouse, and a touch screen through which a user can provide an input. The storage device 916 may be configured to store data, which may include data acquired with an MRI system, magnetic resonance images, calculated contrast concentration curves, estimated quantitative parameters, and/or quantitative parameters maps, whether these data are provided to, or processed by, the processing unit 902. The display 918 may be used to display images and other information, such as magnetic resonance images, patient health data, and so on.

The processing unit 902 can also be in electronic communication with a network 922 to transmit and receive data and other information. The communication port 914 can also be coupled to the processing unit 902 through a switched central resource, for example the communication bus 912. The processing unit can also include temporary storage 925 and a display controller 926. The temporary storage 924 is configured to store temporary information. For example, the temporary storage 924 can be a random access memory.

Computer-executable instructions for accelerating dictionary matching and generation for DCE-MRI perfusion analysis according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly states, are possible and within the scope of the invention.

The invention claimed is:
1. A method for determining quantitative parameters for dynamic contrast-enhanced magnetic resonance (MR) data, the method comprising:
 acquiring a set of contrast-enhanced MR data for a region of interest using a T1-weighted pulse sequence;
 generating at least one contrast concentration curve based on the set of contrast-enhanced MR data;
 accessing a comprehensive dictionary of contrast concentration curves;

generating a grouped dictionary based on the comprehensive dictionary, the grouped dictionary including a plurality of groups, wherein each group includes a plurality of correlated contrast concentration curves and a group representative signal that represents the group;

comparing at least one contrast concentration curve with the group representative signal of each group to select a group;

comparing the at least one contrast concentration curve to the plurality of correlated contrast concentration curves in the selected group to identify at least one quantitative parameter for the at least one concentration curve; and generating a report including the at least one quantitative parameter.

2. The method according to claim 1, wherein the set of contrast-enhanced MR data includes a signal intensity and wherein the at least one contrast concentration curve is generated based on the signal intensity of the set of contrast enhanced MR data.

3. The method according to claim 1, wherein the T1-weighted pulse sequence is a fast spoiled gradient echo pulse sequence.

4. The method according to claim 1, wherein the at least one quantitative parameter includes permeability, perfusion and blood flow.

5. The method according to claim 1, wherein the at least one quantitative parameter is a set of quantitative parameters.

6. A method for determining quantitative parameters for dynamic contrast-enhanced magnetic resonance (MR) data, the method comprising:

acquiring a set of contrast-enhanced MR data for a region of interest using a T1-weighted pulse sequence;

generating at least one contrast concentration curve based on the set of contrast-enhanced MR data;

accessing a compressed dictionary, the compressed dictionary generated by performing a randomized singular value decomposition on a dictionary of concentration curves, the compressed dictionary comprising a series of singular values from the dictionary of concentration curves;

comparing at least one contrast concentration curve with the compressed dictionary to identify at least one quantitative parameter for the at least one contrast concentration curve; and generating a report including the at least one quantitative parameter.

7. The method according to claim 6, wherein the series of singular values are low rank approximations of true values of the concentration curves in the dictionary.

8. The method according to claim 6, wherein the T1-weighted pulse sequence is a fast spoiled gradient echo pulse sequence.

9. The method according to claim 6, wherein the at least one quantitative parameter includes permeability, perfusion and blood flow.

10. The method according to claim 6, wherein the at least one quantitative parameter is a set of quantitative parameters.

11. A method for determining quantitative parameters for dynamic contrast-enhanced magnetic resonance (MR) data, the method comprising:

acquiring a set of contrast-enhanced MR data for a region of interest using a T1-weighted pulse sequence;

generating at least one measured contrast concentration curve based on the set of contrast-enhanced MR data;

providing at least one measured concentration curve to a neural network, the neural network trained using a dictionary of contrast concentration curves as a training data set for a dictionary matching process, each entry in the dictionary of contrast concentration curves having an associated set of quantitative parameters used to generate the dictionary entry, wherein the dictionary of contrast concentration curves is used to train the neural network to generate at least one quantitative parameter associated with the at least one measured concentration curve;

generating the at least one quantitative parameter for the at least one measured contrast concentration curve using the neural network; and generating a report including the at least one quantitative parameter.

12. The method according to claim 11, wherein the neural network generates the at least one quantitative parameter using a supervised learning model.

13. The method according to claim 11, wherein the neural network generated the at least one quantitative parameter using an unsupervised learning model.

14. The method according to claim 11, wherein the T1-weighted pulse sequence is a fast spoiled gradient echo pulse sequence.

15. The method according to claim 11, wherein the at least one quantitative parameter includes permeability, perfusion and blood flow.

16. The method according to claim 11, wherein the at least one quantitative parameter is a set of quantitative parameters.

17. A magnetic resonance imaging system comprising:

a magnet system configured to generate a polarizing magnetic field about at least a portion of a subject;

a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array; and a computer system comprising a graphics processing unit, the computer system programmed to:

access a dictionary of concentration curves;

acquire a set of contrast-enhanced MR data for a region of interest using a T1-weighted pulse sequence;

generate at least one contrast concentration curve based on the set of contrast-enhanced MR data;

using the graphics processing unit, compare at least one contrast concentration curve with the dictionary to identify at least one quantitative parameter for the at least one contrast concentration curve, wherein the comparison is performed as a plurality of operations, each operation performed independently and simultaneously by the graphics processing unit; and generate a report including the at least one quantitative parameter.

18. The system according to claim 17, wherein the graphics processing unit is further configured to generate the dictionary of contrast concentration curves by simulating a plurality of contrast concentration curves.

19. The system according to claim 18, wherein each contrast concentration curve in the dictionary is independent of the other contrast concentration curves in the dictionary and the contrast concentration curves in the dictionary are generated simultaneously using the graphics processing unit.

20. The system according to claim 18, wherein the plurality of contrast concentration curves are generated using a pharmacokinetic model.

21. The method according to claim 17, wherein the at least one quantitative parameter is a set of quantitative parameters.

* * * * *